US011266358B2

(12) United States Patent
Nishijima

(10) Patent No.: US 11,266,358 B2
(45) Date of Patent: Mar. 8, 2022

(54) X-RAY COMPUTED TOMOGRAPHY APPARATUS

(71) Applicant: Canon Medical Systems Corporation, Otawara (JP)

(72) Inventor: Akira Nishijima, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 10 days.

(21) Appl. No.: 16/531,308

(22) Filed: Aug. 5, 2019

(65) Prior Publication Data

US 2020/0037967 A1 Feb. 6, 2020

(30) Foreign Application Priority Data

Aug. 6, 2018 (JP) ............................ JP2018-147916

(51) Int. Cl.

*A61B 6/03* (2006.01)
*A61B 6/00* (2006.01)
*G06N 20/00* (2019.01)

(52) U.S. Cl.

CPC .............. *A61B 6/032* (2013.01); *A61B 6/462* (2013.01); *A61B 6/5205* (2013.01); *A61B 6/5258* (2013.01); *A61B 6/4035* (2013.01); *A61B 6/466* (2013.01); *A61B 6/541* (2013.01); *G06N 20/00* (2019.01)

(58) Field of Classification Search

CPC ......... A61B 6/032; A61B 6/06; A61B 6/4035; A61B 6/4233; A61B 6/462; A61B 6/466; A61B 6/5205; A61B 6/5258; A61B 6/541; G06N 20/00; G01T 1/247

See application file for complete search history.

(56) References Cited

U.S. PATENT DOCUMENTS 6,115,445 A * 9/2000 Lai ......................... A61B 6/032 378/4
6,701,000 B1 * 3/2004 Hsieh .................. G01N 23/046 378/12
10,070,840 B2 9/2018 Hashimoto et al.
(Continued)

FOREIGN PATENT DOCUMENTS

JP 08-243100 A 9/1996
JP 2001 057975 A 3/2001
(Continued)

*Primary Examiner* — Dani Fox
*Assistant Examiner* — Soorena Kefayati
(74) *Attorney, Agent, or Firm* — Oblon, McClelland, Maier & Neustadt, L.L.P.

(57) ABSTRACT

According to one embodiment, an X-ray computed tomography apparatus includes an X-ray detection element, an A/D convertor, a readout switch, and readout control circuitry. The X-ray detection element outputs an electric signal corresponding to a detected X-ray. The A/D convertor A/D-converts the electric signal. The readout switch switches a connection between the X-ray detection element and the A/D convertor. The readout control circuitry acquires, as offset data, data which is output by the A/D convertor in a state where the readout switch is OFF instead of projection data which is output by the A/D convertor according to the electric signal in a state where the readout switch is ON, in a view during a scan.

15 Claims, 8 Drawing Sheets

(56) References Cited

U.S. PATENT DOCUMENTS

| | | | | |
|---|---|---|---|---|
| 2011/0147601 | A1* | 6/2011 | Niekawa | A61B 6/4233 250/370.09 |
| 2012/0091352 | A1* | 4/2012 | Enomoto | H04N 5/32 250/370.08 |
| 2012/0189099 | A1* | 7/2012 | Liu | A61B 6/566 378/62 |
| 2012/0189100 | A1* | 7/2012 | Liu | A61B 6/566 378/62 |
| 2012/0230469 | A1* | 9/2012 | Yamanaka | A61B 6/5205 378/62 |
| 2014/0211910 | A1* | 7/2014 | Subramanian | A61B 6/027 378/5 |
| 2015/0192684 | A1* | 7/2015 | Ito | G01T 7/005 250/362 |
| 2016/0015358 | A1* | 1/2016 | Yagi | H03F 3/45475 378/62 |
| 2016/0242704 | A1* | 8/2016 | Yamazaki | G01T 1/2018 |
| 2017/0095222 | A1* | 4/2017 | Hashimoto | A61B 6/4488 |
| 2017/0231589 | A1* | 8/2017 | Fujii | A61B 6/5205 378/20 |
| 2017/0278277 | A1* | 9/2017 | Morf | A61B 6/032 |
| 2017/0332990 | A1* | 11/2017 | Kudo | A61B 6/4233 |
| 2018/0116596 | A1* | 5/2018 | Sanders, III | A61B 5/721 |
| 2018/0256123 | A1* | 9/2018 | Maruta | A61B 6/4283 |
| 2019/0216413 | A1* | 7/2019 | Jin | A61B 6/4208 |
| 2019/0328348 | A1* | 10/2019 | De Man | A61B 6/5205 |
| 2020/0077036 | A1* | 3/2020 | Koeda | A61B 6/5205 |

FOREIGN PATENT DOCUMENTS

| | | | |
|---|---|---|---|
| JP | 2002-534205 | A | 10/2002 |
| JP | 2014-138660 | A | 7/2014 |
| JP | 2017-064288 | A | 4/2017 |

* cited by examiner

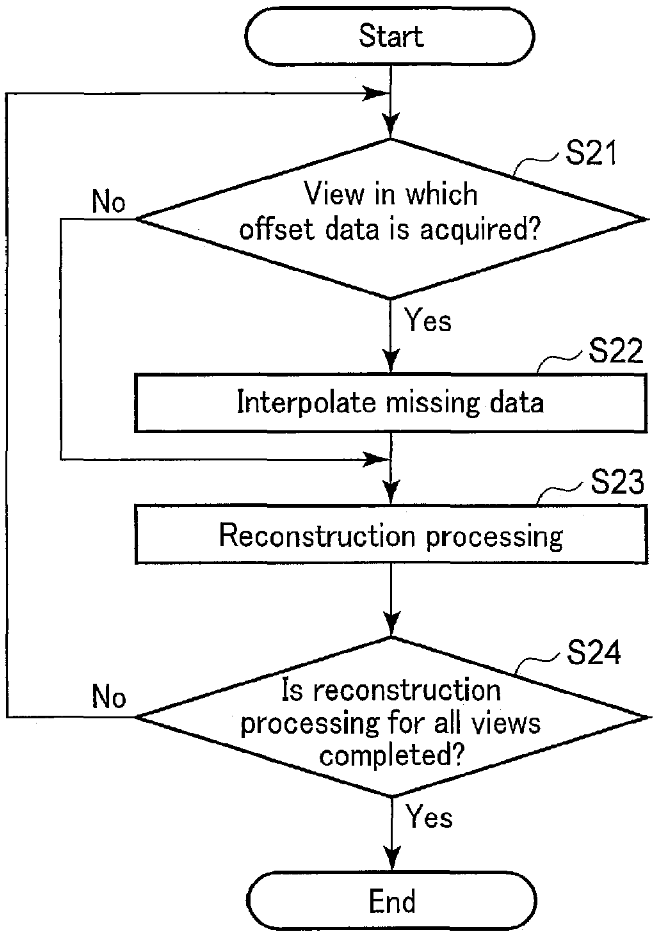
F I G. 6

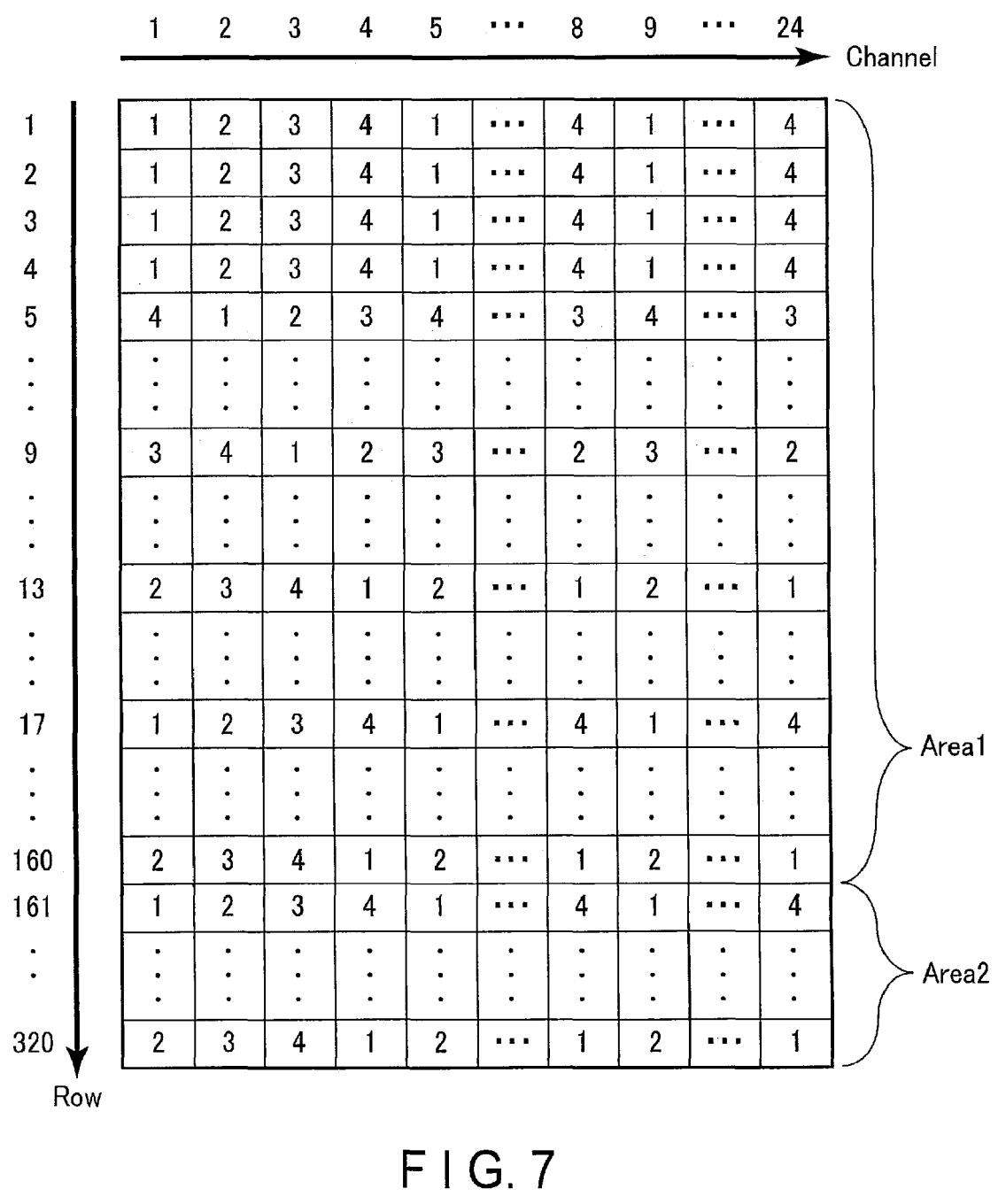

| Row \ Channel | 1 | 2 | 3 | 4 | 5 | ··· | 8 | 9 | ··· | 24 | |
|---|---|---|---|---|---|---|---|---|---|---|---|
| 1 | 1 | 2 | 3 | 4 | 1 | ··· | 4 | 1 | ··· | 4 | Area1 |
| 2 | 1 | 2 | 3 | 4 | 1 | ··· | 4 | 1 | ··· | 4 | |
| 3 | 1 | 2 | 3 | 4 | 1 | ··· | 4 | 1 | ··· | 4 | |
| 4 | 1 | 2 | 3 | 4 | 1 | ··· | 4 | 1 | ··· | 4 | |
| 5 | 4 | 1 | 2 | 3 | 4 | ··· | 3 | 4 | ··· | 3 | |
| ⋮ | ⋮ | ⋮ | ⋮ | ⋮ | ⋮ | ⋮ | ⋮ | ⋮ | ⋮ | ⋮ | |
| 9 | 3 | 4 | 1 | 2 | 3 | ··· | 2 | 3 | ··· | 2 | |
| ⋮ | ⋮ | ⋮ | ⋮ | ⋮ | ⋮ | ⋮ | ⋮ | ⋮ | ⋮ | ⋮ | |
| 13 | 2 | 3 | 4 | 1 | 2 | ··· | 1 | 2 | ··· | 1 | |
| ⋮ | ⋮ | ⋮ | ⋮ | ⋮ | ⋮ | ⋮ | ⋮ | ⋮ | ⋮ | ⋮ | |
| 17 | 1 | 2 | 3 | 4 | 1 | ··· | 4 | 1 | ··· | 4 | |
| ⋮ | ⋮ | ⋮ | ⋮ | ⋮ | ⋮ | ⋮ | ⋮ | ⋮ | ⋮ | ⋮ | |
| 160 | 2 | 3 | 4 | 1 | 2 | ··· | 1 | 2 | ··· | 1 | |
| 161 | 1 | 2 | 3 | 4 | 1 | ··· | 4 | 1 | ··· | 4 | Area2 |
| ⋮ | ⋮ | ⋮ | ⋮ | ⋮ | ⋮ | ⋮ | ⋮ | ⋮ | ⋮ | ⋮ | |
| 320 | 2 | 3 | 4 | 1 | 2 | ··· | 1 | 2 | ··· | 1 | |

Channel → ; Row ↓

FIG. 7

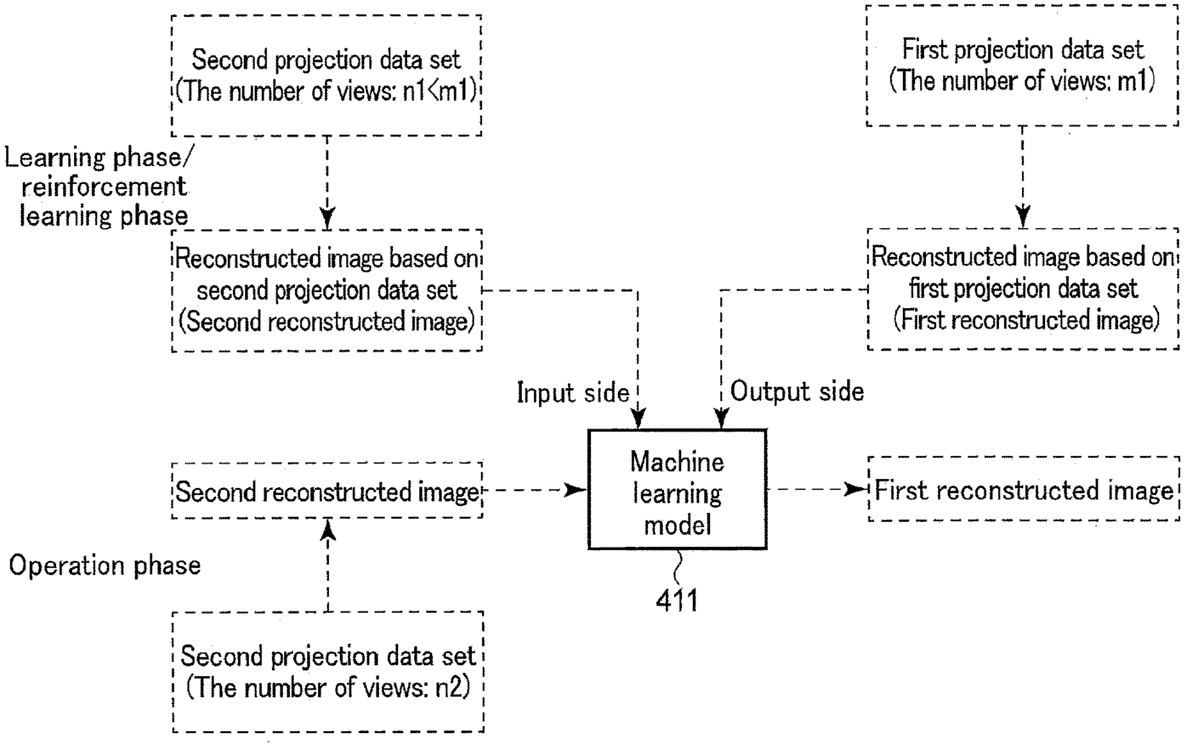
F I G. 10

X-RAY COMPUTED TOMOGRAPHY APPARATUS

CROSS-REFERENCE TO RELATED APPLICATIONS

This application is based upon and claims the benefit of priority from the prior Japanese Patent Application No. 2018-147916, filed Aug. 6, 2018 the entire contents of which are incorporated herein by reference.

FIELD

Embodiments described herein relate generally to an X-ray computed tomography apparatus.

BACKGROUND

In an X-ray computed tomography (CT) apparatus, there is a technique which acquires offset data before the start of a scan or after the end of a scan, and corrects an offset component of an output value of an X-ray detection element or an analog-digital convertor (A/D convertor). However, if the scan is performed for a long time, the drift component generated during the scan may have a large fluctuation so that it cannot be accurately corrected.

BRIEF DESCRIPTION OF THE DRAWINGS

FIG. 6 is a flowchart showing an example of reconstruction processing performed by the X-ray computed tomography apparatus of FIG. 1;

FIG. 7 is a diagram illustrating another example of readout switches which turn into an OFF state in the data acquisition processing of FIG. 3;

FIG. 10 is a diagram illustrating interpolation of missing data using a machine learning model in the reconstruction processing of FIG. 6.

DETAILED DESCRIPTION

Figure 1:
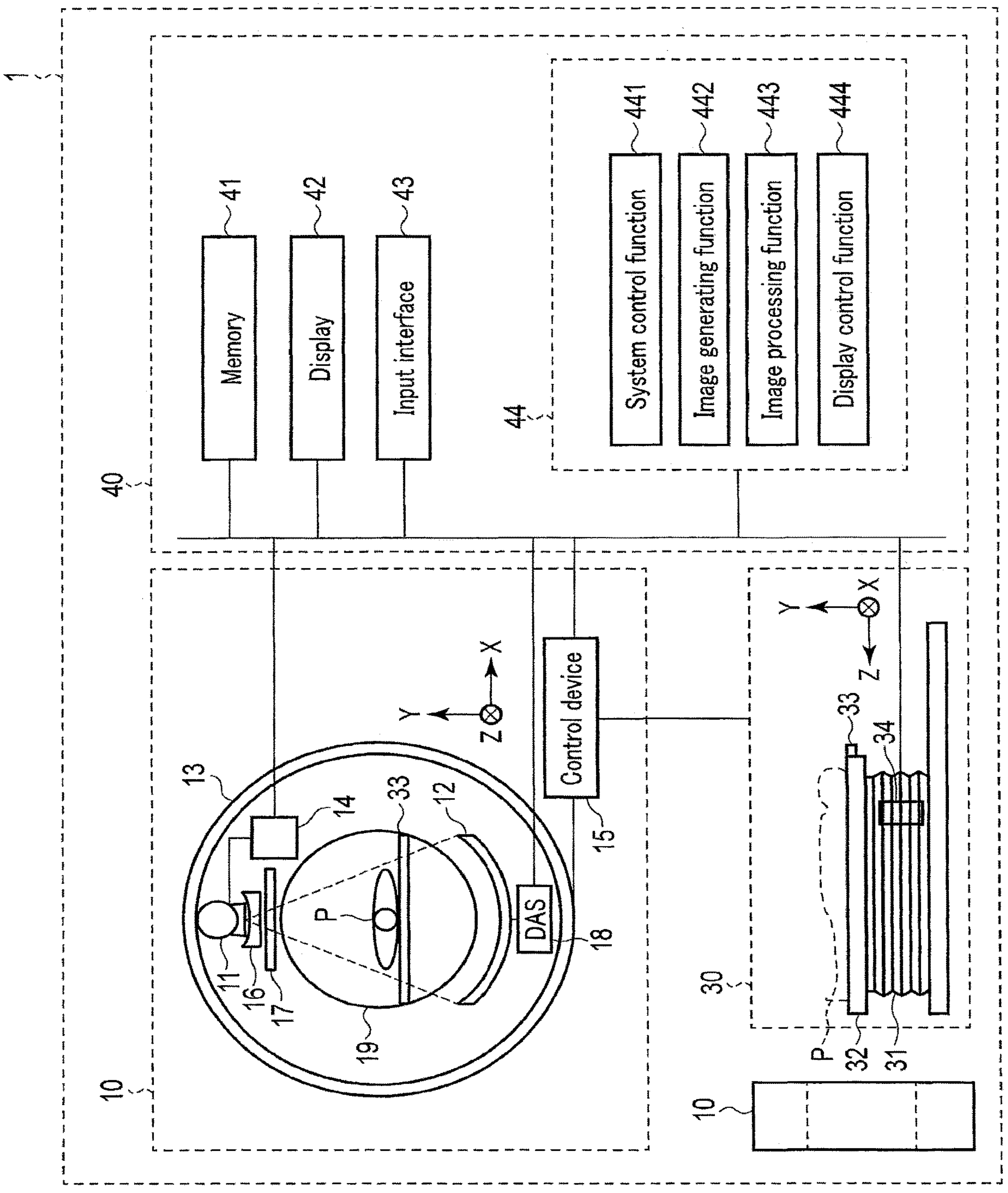
FIG. 1 is a diagram showing an example of a configuration of an X-ray computed tomography apparatus according to an embodiment.

In general, according to one embodiment, An X-ray computed tomography apparatus includes an X-ray detection element, an A/D convertor, a readout switch, and readout control circuitry. The X-ray detection element outputs an electric signal corresponding to a detected X-ray.

The A/D convertor A/D-converts the electric signal. The readout switch switches a connection between the X-ray detection element and the A/D convertor. The readout control circuitry acquires, as offset data, data which is output by the A/D convertor in a state where the readout switch is OFF instead of projection data which is output by the A/D convertor according to the electric signal in a state where the readout switch is ON, in a view during a scan.

Hereinafter, a radiation diagnostic apparatus according to the present embodiment will be described with reference to the accompanying drawings. In the description below, structural elements having the same or substantially the same functions as earlier described ones in preceding diagrams are denoted by like reference numerals, and an overlapping description will be given only where necessary. Even when the same parts are represented, the sizes and proportions may be different from each other in different drawings.

The radiation diagnostic apparatus according to the present embodiment is applicable to an X-ray computed tomography apparatus, an X-ray diagnostic apparatus, and a nuclear medicine diagnostic apparatus. Hereinafter, a radiation detector according to the present embodiment will described as an X-ray detector that detects an X-ray. The radiation diagnostic apparatus according to the present embodiment will described as an X-ray computed tomography apparatus mounted with the X-ray detector.

The X-ray computed tomography apparatus (CT apparatus) may be of various types such as third generation CT and fourth generation CT, and either type can be applied to the present embodiment. The third generation CT refers to Rotate/Rotate-Type in which an X-ray tube and a detector are integrally rotated around a subject. The fourth generation CT refers to Stationary/Rotate-Type in which multiple X-ray detection elements are arrayed in a ring shape, and only an X-ray tube is rotated around a subject.

FIG. 1 is a diagram showing an example of a configuration of an X-ray computed tomography apparatus 1 according to the present embodiment. In the X-ray computed tomography apparatus 1, X-rays are radiated on a subject P from an X-ray tube 11, and the radiated X-rays are detected by an X-ray detector 12. Based on the output from the X-ray detector 12, the X-ray computed tomography apparatus 1 generates a CT image relating to the subject P.

As illustrated in FIG. 1, the X-ray computed tomography apparatus 1 includes a gantry 10, a bed 30 and a console 40. For convenience of explanation, a plurality of gantries 10 are illustrated in FIG. 1. The gantry 10 is a scan device including a configuration for X-ray CT scan of the subject P. The bed 30 is a convey device for placing thereon the subject P that is the target of X-ray CT scan and for aligning the subject P. The console 40 is a computer which controls the gantry 10. For example, the gantry 10 and bed 30 are installed in a CT examination room, and the console 40 is installed in a control room adjacent to the CT examination room. The gantry 10, bed 30 and console 40 are communicably connected by wire or by radio. Note that the console 40 may not necessarily be installed in the control room. For example, the console 40 may be installed in the same room as the gantry 10 and bed 30. Besides, the console 40 may be built in the gantry 10.

As illustrated in FIG. 1, the gantry 10 includes the X-ray tube 11, the X-ray detector 12, a rotation frame 13, an X-ray high voltage generator 14, a control device 15, a wedge 16, a collimator 17, and data acquisition circuitry (DAS: Data Acquisition System) 18.

The X-ray tube 11 radiates X-rays on the subject P. Specifically, the X-ray tube 11 includes a cathode which generates thermions, an anode which receives the thermions flying from the cathode and generates X-rays, and a vacuum tube which holds the cathode and anode. The X-ray tube 11 is connected to the X-ray high voltage generator 14 via a high-voltage cable. A tube voltage is applied between the cathode and anode by the X-ray high voltage generator 14. By the application of the tube voltage, thermions fly from the cathode toward the anode. By the thermions flying from the cathode toward the anode, a tube current flows. By the application of high voltage and the supply of filament current from the X-ray high voltage generator 14, thermions fly from the cathode (filament) toward the anode (target), and X-rays are generated by the thermions impinging on the anode. For example, the X-ray tube 11 may be a rotating-anode-type X-ray tube which generates X-rays by radiating thermions on a rotating anode.

The hardware for generating X-rays is not limited to the X-ray tube 11. For example, a fifth generation system may be used for generating X-rays without the X-ray tube 11. The fifth generation system includes a focus coil which focuses an electron beam generated from an electron gun, a deflection coil which electromagnetically deflects it, and a target ring which surrounds the half circumference of the subject P and generates an X-ray by collision of a deflected electron beam thereon.

The X-ray detector 12 detects X-rays which are radiated from the X-ray tube 11 and pass through the subject P, and outputs to the data acquisition circuitry 18 an electric signal corresponding to the dose of the detected X-rays. The X-ray detector 12 has a configuration in which a plurality of X-ray detection element rows, each including a plurality of X-ray detection elements arranged in a channel direction, are arranged in a slice direction (row direction). The X-ray detector 12 is an indirect-conversion-type detector including a grid, a scintillator array and an optical sensor array. The scintillator array includes a plurality of scintillators. The scintillator outputs light of an amount corresponding to an incident X-ray amount. The grid includes an X-ray shield plate which is disposed on the X-ray incident surface side of the scintillator array, and absorbs scattered X-rays. The grid may also be referred to as a collimator (one-dimensional collimator or two-dimensional collimator). The optical sensor array converts the light from the scintillator to an electric signal corresponding to the amount of light from the scintillator. For example, a photodiode is used as the optical sensor. The X-ray detector 12 may be a direct-conversion-type detector.

The rotation frame 13 is an annular frame which supports the X-ray tube 11 and X-ray detector 12 such that the X-ray tube 11 and X-ray detector 12 are rotatable around a rotational axis (Z-axis). Specifically, the rotation frame 13 supports the X-ray tube 11 and X-ray detector 12 such that the X-ray tube 11 and X-ray detector 12 are opposed to each other. The rotation frame 13 is supported on a stationary frame (not shown) such that the rotation frame 13 is rotatable around the rotational axis. The control device 15 causes the rotation frame 13 to rotate around the rotational axis by the control device 15, thereby rotating the X-ray tube 11 and X-ray detector 12 around the rotational axis. The rotation frame 13 rotates at a fixed angular velocity around the rotational axis by receiving driving force from a driving mechanism of the control device 15. A field of view (FOV) is set in a bore 19 of the rotation frame 13.

In the present embodiment, the rotational axis of the rotation frame 13 in a non-tilt state or the longitudinal direction of the table top 33 of the bed 30 is defined as a Z-axis direction; a direction orthogonal to the Z-axis direction and horizontal to the floor surface is defined as an X-axis direction; and a direction orthogonal to the Z-axis direction and perpendicular to the floor surface is defined as a Y-axis direction.

The X-ray high voltage generator 14 includes a high voltage generation device and an X-ray control device. The high voltage generation device includes electric circuitry such as a transformer and a rectifier, and generates a high voltage which is applied to the X-ray tube 11 and a filament current which is supplied to the X-ray tube 11. The X-ray control device controls an output voltage according to an X-ray radiated from the X-ray tube 11. The high voltage generation device may adopt either a transformer method or an inverter method. The X-ray high voltage generator 14 may be provided in the rotation frame 13 in the gantry 10, or may be provided in the stationary frame (not shown) in the gantry 10.

The wedge 16 adjusts the dose of X-rays which are radiated on the subject P. Specifically, the wedge 16 attenuates X-rays such that the dose of X-rays radiated on the subject P from the X-ray tube 11 may have a predetermined distribution. For example, as the wedge 16, a metal plate of aluminum or the like, such as a wedge filter or a bow-tie filter, is used.

The collimator 17 restricts the range of radiation of X-rays which have passed through the wedge 16. The collimator 17 slidably supports a plurality of lead plates which shield X-rays, and adjusts the form of a slit which is formed by the lead plates. The collimator 17 may also be referred to as an X-ray diaphragm.

The data acquisition circuitry 18 reads out an electric signal corresponding to the dose of X-rays, which were detected by the X-ray detector 12, from the X-ray detector 12. The data acquisition circuitry 18 amplifies the read electric signal, and integrates electric signals over a view period, thereby acquiring detection data having a digital value corresponding to the dose of X-rays over the view period. The detection data is called "projection data". The data acquisition circuitry 18 is realized by an ASIC (Application Specific Integrated Circuit) on which a circuitry element that can generate projection data is mounted. The projection data is transmitted to the console 40 via a non-contact data transmission device or the like.

Although the integral-type X-ray detector 12 and the X-ray computed tomography apparatus 1 on which the integral-type X-ray detector 12 is mounted are described as an example in the present embodiment, the technique according to the present embodiment may also be applied to a photon counting-type X-ray detector or an X-ray computed tomography apparatus on which the photon counting-type X-ray detector is mounted.

The control device 15 controls the X-ray high voltage generator 14 and data acquisition circuitry 18 in order to execute X-ray CT imaging in accordance with a system control function 441 by processing circuitry 44 of the console 40. The control device 15 includes processing circuitry including a CPU (Central Processing Unit) or an MPU (Micro Processing Unit) or the like, and a driving device such as a motor and an actuator or the like. The processing circuitry includes, as hardware resources, a processor such as a CPU, and a memory such as a ROM (Read Only Memory) or RAM (Random Access Memory). In addition, the control device 15 may be realized by an ASIC or an FPGA (Field Programmable Gate Array). Further, the control device 15 may be realized by a CPLD (Complex Programmable Logic Device) or an SPLD (Simple Programmable Logic Device). The control device 15 has a function of receiving an input signal from an input interface 43 provided on the console 40 or the gantry 10 as described later, and controlling the operation of the gantry 10 and the bed 30. For example, upon a receiving an input signal, the control device 15 performs control to rotate the rotation frame 13, tilt the gantry 10, or operate the bed 30 and the table top 33. The control device 15 achieves the control of tilting the gantry 10 by rotating the rotation frame 13 around the axis in parallel to the X-axis direction based on inclined angle (tilt angle) information input from the input interface mounted on the gantry 10. The control device 15 may be provided in the gantry 10, or may be provided in the console 40.

The bed 30 includes a base 31, a support frame 32, the table top 33, and a bed actuator 34. The base 31 is installed on the floor surface. The base 31 is a structure which supports the support frame 32 such that the support frame 32 is movable in the vertical direction (Y-axis direction) relative to the floor surface. The support frame 32 is a frame provided on an upper part of the base 31. The support frame 32 supports the table top 33 such that the table top 33 is slidable along the rotational axis (Z-axis). The table top 33 is a plate with flexibility, on which the subject P is placed.

The bed actuator 34 is housed in the bed 30. The bed actuator 34 is a motor or an actuator which generates driving force for moving the support frame 32 and table top 33 on which the subject P is placed. The bed actuator 34 operates in accordance with the control by the console 40, etc.

The console 40 includes a memory 41, a display 42, an input interface 43 and processing circuitry 44. Data communication between the memory 41, display 42, input interface 43 and processing circuitry 44 is executed via a bus (BUS). Although the console 40 is described as a separate body from the gantry 10, the console 40 or some components of the console 40 may be included in the gantry 10.

The memory 41 is a storage device which stores various information, such as an HDD (Hard Disk Drive), an SSD (Solid State Drive) or an integrated circuit storage device. The memory 41 stores, for example, projection data and reconstructed image data. The memory 41 may be, aside from the HDD, SSD or the like, a portable storage medium such as a CD (Compact Disc), a DVD (Digital Versatile Disc) or a flash memory. The memory 41 may be a drive unit which reads/writes various information from/to a semiconductor memory device or the like, such as a flash memory or a RAM (Random Access Memory). Besides, a storage area of the memory 41 may exist in the X-ray computed tomography apparatus 1, or may exist in an external storage device connected over a network. The memory 41 stores a database as described later.

The display 42 displays various kinds of information. The display 42 outputs, for instance, a medical image (CT image) generated by the processing circuitry 44, and a GUI (Graphical User Interface) or the like for accepting various kinds of operations from an operator. Any of various types of display may be used as the display 42 as appropriate. For example, a liquid crystal display (LCD), a CRT (Cathode Ray Tube) display, an organic electro luminescence display (OELD), or a plasma display may be used as the display 42. The display 42 may be provided on the gantry 10. The display 42 may be a desktop-type display, or may be provided as a tablet terminal or the like capable of wireless communication with the main body of the console 40.

The input interface 43 accepts various kinds of input operations from the operator, converts the accepted input operations to electric signals, and outputs the electric signals to the processing circuitry 44. For example, the input interface 43 receives, from the operator, an acquisition condition for acquiring projection data, a reconstruction condition for reconstructing a CT image, an image processing condition for generating a post-processed image from a CT image, and the like. As the input interface 43, for example, use can be made of, as needed, a mouse, a keyboard, a trackball, a switch, a button, a joystick, a touchpad, a touch panel display, etc. Note that in the present embodiment, the input interface 43 is not limited to a device including a physical operation part, such as a mouse, a keyboard, a trackball, a switch, a button, a joystick, a touchpad, a touch panel display, etc. Examples of the input interface 43 include processing circuitry of an electric signal, which receives an electric signal corresponding to an input operation from an external input device, which is provided separately from the apparatus, and outputs the received electric signal to the processing circuitry 44. The input interface 43 may be provided on the gantry 10. The input interface 43 may be provided as a tablet terminal or the like capable of wireless communication with the main body of the console 40.

The processing circuitry 44 controls the operation of the entirety of the X-ray computed tomography apparatus 1 in accordance with an electric signal of an input operation which is output from the input interface 43. The processing circuitry 44 generates image data based on an electric signal which is output from the X-ray detector 12. For example, the processing circuitry 44 includes, as hardware resources, a processor such as a CPU, an MPU, a GPU (Graphics Processing Unit), etc., and a memory such as a ROM, a RAM, etc. The processing circuitry 44 executes a system control function 441, an image generating function 442, an image processing function 443, a display control function 444, and the like, by the processor which executes a program developed on the memory. Note that the embodiment is not limited to the case in which the respective functions 441 to 444 are realized by single processing circuitry. Processing circuitry may be composed by combining a plurality of independent processors, and the respective processors may execute programs, thereby realizing the functions 441 to 444.

In the system control function 441, the processing circuitry 44 controls the X-ray high voltage generator 14, control device 15 and data acquisition circuitry 18 in order to execute X-ray CT scan.

In the image generating function 442, the processing circuitry 44 applies preprocesses, such as a logarithmic conversion process, an offset correction process, an inter-channel sensitivity correction process and beam hardening correction, to the projection data which is output from the data acquisition circuitry 18. In addition, in the image generating function 442, the processing circuitry 44 applies reconstruction processing, which uses a filtered back projection method or an iterative approximation reconstruction method, to the preprocessed projection data, thereby generating a CT image.

In the image processing function 443, the processing circuitry 44 converts the CT image, which is generated by the image generating function 442, to cross section image data of an arbitrary cross section or rendered image data from an arbitrary viewpoint direction. The conversion is performed based on an input operation which was accepted from the operator via the input interface 43. For example, the processing circuitry 44 applies three-dimensional image processing, such as volume rendering, surface rendering, image value projection processing, MPR (Multi-Planer Reconstruction) processing or CPR (Curved MPR) processing to the CT image data, thereby generating rendered image data from an arbitrary viewpoint direction. Such generation of rendered image data from an arbitrary viewpoint direction may be performed directly by the image generating function 442.

In the display control function 444, the processing circuitry 44 displays an image on the display 42 based on various kinds of image data generated by the image processing function 443. Images to be displayed on the display 42 include a CT image based on CT image data, a cross section image based on cross section image data of an arbitrary cross section, and a rendered image from an arbitrary viewpoint direction based on rendered image data from the arbitrary viewpoint direction. Further, images to be displayed on the display 42 include an image for displaying an operation screen.

Although the console 40 as a single console executes a plurality of functions in the above description, a plurality of functions may be executed by different consoles. For example, functions of the processing circuitry 44 such as the image generating function 442 may be distributed. For example, the image generating function 442 may be divided into a preprocessing function and a reconstruction processing function.

The processing circuitry 44 may not necessarily be included in the console 40, and may be included in an integrated server which collectively performs processing on detection data obtained by a plurality of medical diagnostic imaging apparatuses.

The post-processing may be performed by the console 40 or an external workstation. It may also be performed by both the console 40 and the external workstation at the same time.

The technique according to the present embodiment is applicable to a single-tube-type X-ray computed tomography apparatus, as well as a so-called multi-tube-type X-ray computed tomography apparatus in which X-ray tubes and X-ray detectors are as plural pairs mounted on rotary rings.

Figure 2:
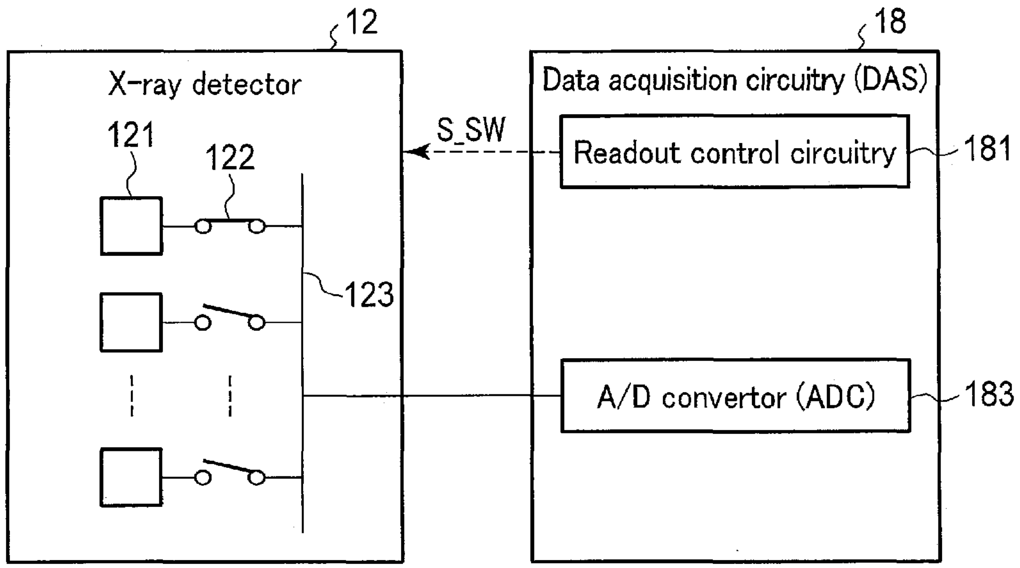
FIG. 2 is a diagram illustrating an example of a configuration of components related to acquisition of offset data in the X-ray computed tomography apparatus of FIG. 1.

Hereinafter, acquisition of offset data by the X-ray computed tomography apparatus 1 according to the present embodiment will be described in more detail with reference to the drawings. FIG. 2 is a diagram illustrating an example of a configuration of components related to acquisition of offset data in the X-ray computed tomography apparatus 1 of FIG. 1.

It is assumed that the X-ray computed tomography apparatus 1 according to the present embodiment is configured to read out electric signals from the X-ray detector 12 in a sequential readout method.

The X-ray detector 12 according to the present embodiment includes a plurality of X-ray detector modules (not shown). The plurality of X-ray detector modules are tiled in a channel direction. Each X-ray detector module is provided with an optical sensor array and readout circuitry.

The optical sensor array outputs an electric signal corresponding to an incident X-ray. Electric signal output is performed at timing according to a switch signal S_SW which is input to the optical sensor array. The optical sensor array has a structure in which a plurality of X-ray detection elements 121 are arranged two-dimensionally in the channel direction and in the row direction. Each X-ray detection element 121 outputs an electric signal corresponding to a detected X-ray. The optical sensor array is an example of the X-ray detection element array. The readout circuitry includes a plurality of readout switches 122 and a read line 123. In FIG. 2, only some of the plurality of X-ray detection elements 121 are schematically shown.

Each of the plurality of readout switches 122 is a switching element which is driven based on a switch signal S_SW. Each of the plurality of readout switches 122 is, for example, MOS-type field effect transistor (Metal Oxide Semiconductor Field Effect Transistor: MOS-FET) or the like. As shown in FIG. 2, a plurality of X-ray detection elements 121 are connected to the read line 123 via the plurality of readout switches 122. More specifically, the plurality of readout switches 122 are connected to the plurality of X-ray detection elements 121 respectively. Each of the readout switches 122 is connected to the read line 123. Each of the plurality of readout switches 122 receives a switch signal S_SW as input from a readout control circuitry 181 of the data acquisition circuitry 18. The plurality of readout switches 122 sequentially allows conduction between the plurality of X-ray detection elements 121 and the read line 123 at timing according to switch signals S_SW. Accordingly, each of the plurality of readout switches 122 switches connection between the X-ray detection elements 121 and an A/D convertor 183 between on and off. Electric signals which are read out sequentially from the plurality of X-ray detection elements 121 are output to the A/D convertor 183 of the data acquisition circuitry 18 via the read line 123.

Hereinafter, with respect to each readout switch 122, a state where conduction is allowed between the respective X-ray detection element 121 and the read line 123 is referred to as ON state, and a state where conduction is not allowed between the respective X-ray detection element 121 and the read line 123 is referred to as OFF state.

It is assumed that the data acquisition circuitry 18 according to the present embodiment is configured to read out electric signals from the X-ray detector 12 in the sequential readout method. The data acquisition circuitry 18 includes the readout control circuitry 181 and the A/D convertor (ADC) 183.

The readout control circuitry 181 generates switch signals S_SW. The readout control circuitry 181 outputs the generated switch signals S_SW to the plurality of readout switches 122. The switch signals S_SW drive the plurality of readout switches 122. Switch signal S_SW includes a first switch signal for acquisition of projection data, and a second switch signal for acquisition of offset data. First switch signals are control signals for controlling operation of the plurality of readout switches 122 so that electric signals are read out from the plurality of X-ray detection elements 121 at predetermined timing in the sequential readout method, in a view for acquisition of projection data. First switch signals can also be represented as signals for controlling readout timing and charge integration time with respect to the plurality of X-ray detection elements 121. Second switch signals are control signals for controlling operation of the plurality of readout switches 122, in a view for acquisition of offset data. Second switch signals can also be represented as signals for controlling timing of offset data acquisition with respect to the A/D convertor 183.

In the view for acquisition of offset data, offset data is acquired at timing corresponding to some of the X-ray detection elements 121, and projection data is acquired with respect to some other X-ray detection elements 121. Therefore, Second switch signals may also be represented as signals for controlling readout timing and charge integration time with respect to a plurality of X-ray detection elements 121.

The A/D convertor 183 A/D-converts an electric signal. The A/D convertor 183 is connected to the plurality of X-ray detection elements 121 via the plurality of readout switches 122. In other words, the A/D convertor 183 is provided corresponding to each of the plurality of X-ray detection elements 121. The A/D convertor 183 outputs projection data or offset data at predetermined timing. At timing with respect to any X-ray detection element 121, when the readout switch 122 is in ON state, the output of the A/D convertor 183 is projection data corresponding to a read electric signal. At timing with respect to any X-ray detection element 121, when the readout switch 122 is in OFF state, the output of the A/D convertor 183 is offset data. Thus, offset data includes a drift component of the A/D convertor 183.

Figure 3:
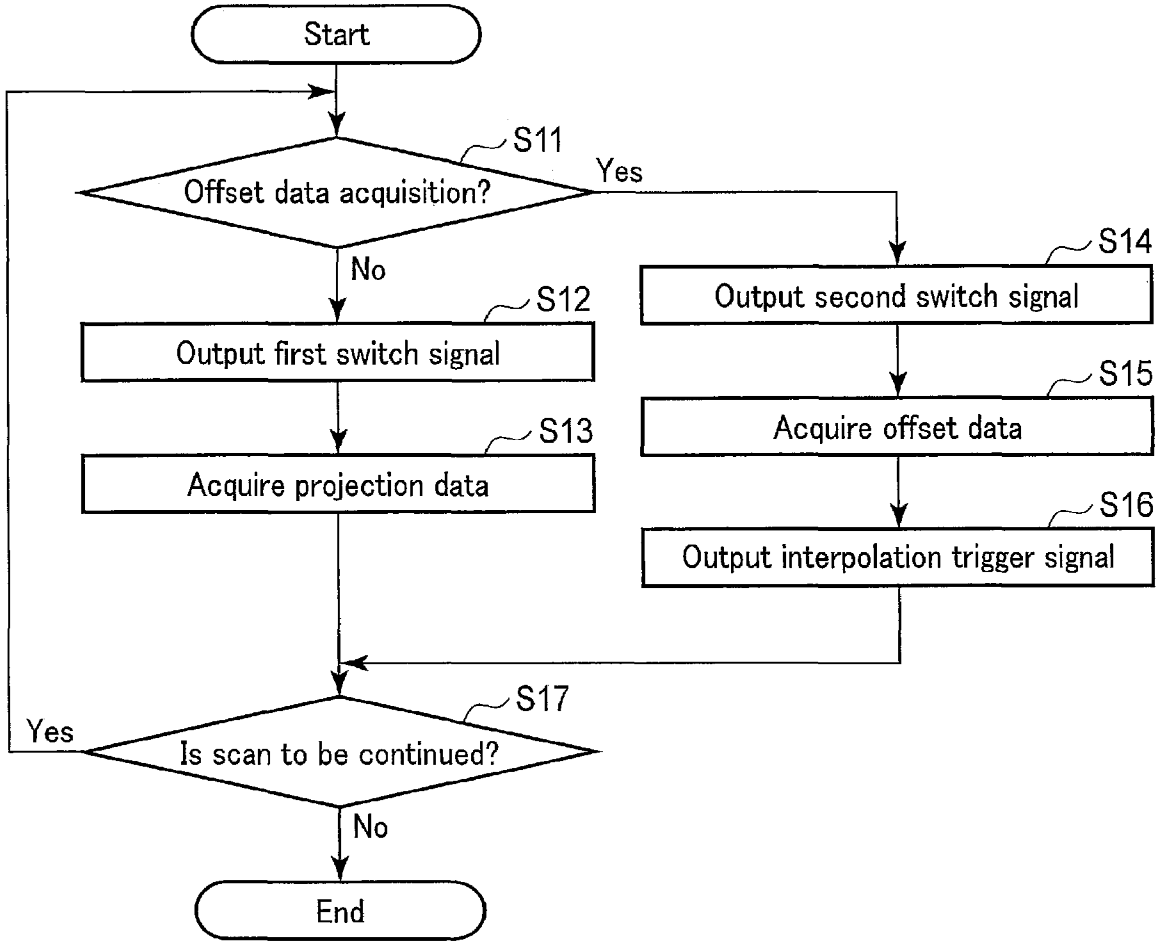
FIG. 3 is a flowchart showing an example of data acquisition processing performed by the X-ray computed tomography apparatus of FIG. 1.

Next, operation about acquisition of offset data by the X-ray computed tomography apparatus 1 according to the present embodiment will be described with reference to FIG. 3. FIG. 3 is a flowchart showing an example of data acquisition processing performed by the X-ray computed tomography apparatus 1.

The following description is about operation when an instruction to start continuous scanning is given after offset data is acquired before the start of the scan. Offset data before the start of the scan is acquired as follows: During rotation of the rotation frame 13 in a state where X-rays are stopped, the X-ray detection element 121 and the A/D convertor 183 are connected by the readout switch 122, and an electric signal is read out from the X-ray detection element 121 and converted to digital data. Thus, the offset data before the start of the scan includes an offset component of the X-ray detection element 121. On the other hand, offset data during a scan as described below is acquired as follows: During rotation of the rotation frame 13 in an X-ray exposure state, the X-ray detection element 121 and the A/D convertor 183 are disconnected by the readout switch 122, and an electric signal during the disconnection is converted to digital data.

In step S11, the readout control circuitry 181 determines whether the view is for acquisition of offset data. In this determination, for example, if a scan has been continued for a preset certain time or more from a scan start time point or from a time point of previous offset data acquisition, it is determined that the view is for acquisition of offset data. A threshold for this determination is stored in, for example, the memory 41. The certain time is, for example, calculated experimentally in advance. The process proceeds to step S14 if it is determined that the view is for acquisition of offset data, and proceeds to step S12 if not.

Alternatively, it may be determined that the view is for acquisition of offset data at a preset certain cycle or timing. Alternatively, it may be determined that the view is for acquisition of offset data, for example, when the variation amount of the temperature or output of the A/D convertor 183 exceeds a predetermined threshold.

There may also be a case where a long scan time is supposed before the start of the scan, such as a whole body scan. For example, when a scan mode and a scan region are selected, timing of acquiring offset data and the like may also be determined. In other words, a scan plan including timing of acquiring offset data may be prepared. In this case, determination processing in step S11 may not necessarily be performed.

In step S12, the readout control circuitry 181 outputs the first switch signal for projection data acquisition to the plurality of readout switches 122. In step S13, the readout control circuitry 181 acquires, as projection data, output of the A/D convertor 183 corresponding to an electric signal which is read out in the ON state of readout switch 122. Thereafter, the process proceeds to step S17.

In step S14, the readout control circuitry 181 outputs the second switch signal for offset data acquisition to the plurality of readout switches 122. In step S15, the readout control circuitry 181 acquires, as offset data, output of the A/D convertor 183 at a time when the readout switch 122 is in the OFF state. Details of offset data acquisition according to the present embodiment will be described later. In step S16, the readout control circuitry 181 outputs to the processing circuitry 44, an interpolation trigger signal which indicates the view of interest is a view in which offset data is acquired. Thereafter, the process proceeds to step S17.

There may also be a case where reconstruction processing is performed after the data acquisition processing ends. In this case, in step S16, the readout control circuitry 181 may record in the memory 41 or the like that the view is a view in which offset data is acquired.

In step S17, the readout control circuitry 181 determines whether the scan is to be continued. If it is determined that the scan is to be continued, the process returns to step S11, and repeats step S11 through step S17. If it is not determined that the scan is to be continued in step S17, the process terminates the data acquisition processing.

Figure 4:
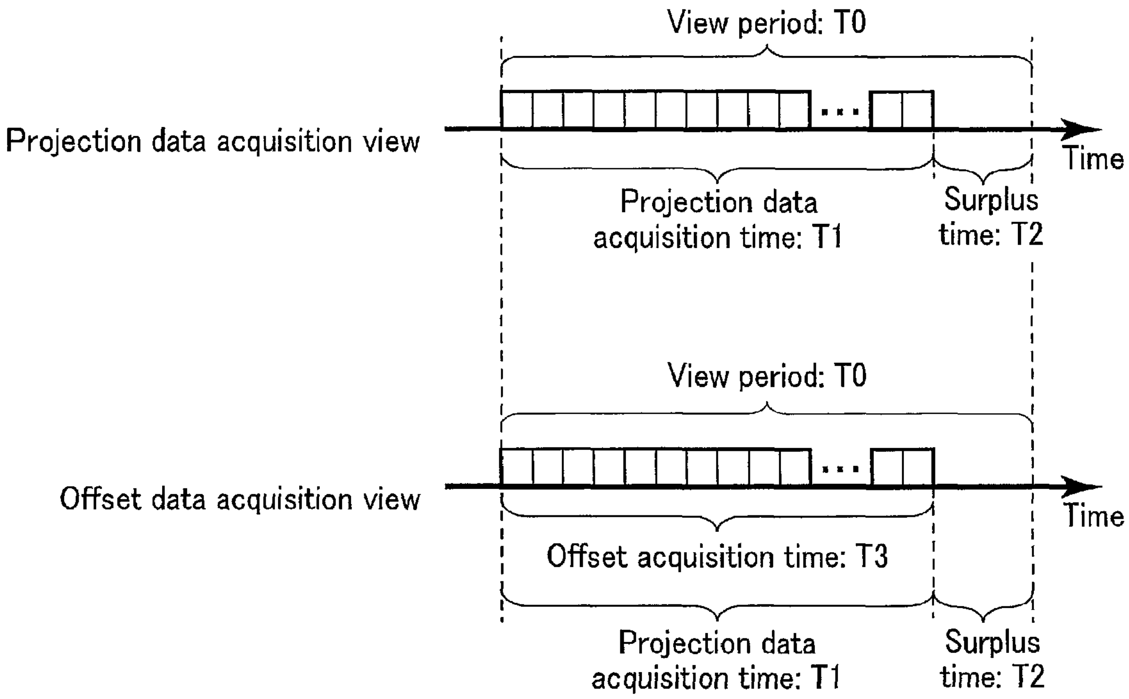
FIG. 4 is a diagram illustrating an example of a time of acquisition of offset data performed in the configuration of FIG. 2.

A time of acquisition of offset data according to the present embodiment will now be described with reference to FIG. 4. FIG. 4 is a diagram illustrating an example of a time of acquisition of offset data in the X-ray computed tomography apparatus 1 according to the present embodiment.

As shown in FIG. 4, in a projection data acquisition view, for each view period T0, projection data acquisition time T1 and a surplus time T2 are provided. A view period T0 used herein is a time for each view. Projection data acquisition time T1 includes a time for reading out electric signals from the X-ray detection elements 121, a time for applying A/D conversion to the electric signals, and a time for acquiring projection data. Surplus time T2 includes a time for the other processing. Surplus time T2 includes a time reserved for supporting a scan having more rows and the like. On the other hand, in an offset data acquisition view, offset data acquisition time T3 is provided at timing corresponding to the projection data acquisition time T1 in the projection data acquisition view. Specifically, in the X-ray computed tomography apparatus 1 according to the present embodiment, at timing when an electric signal is read out from each X-ray detection element 121 in the view for acquisition of projection data, the readout switch 122 connected to the respective X-ray detection element 121 is turned into the OFF state. The readout control circuitry 181 acquires, as offset data, output of the A/D convertor 183 at a time when the readout switch 122 is in the OFF state.

Figure 5:
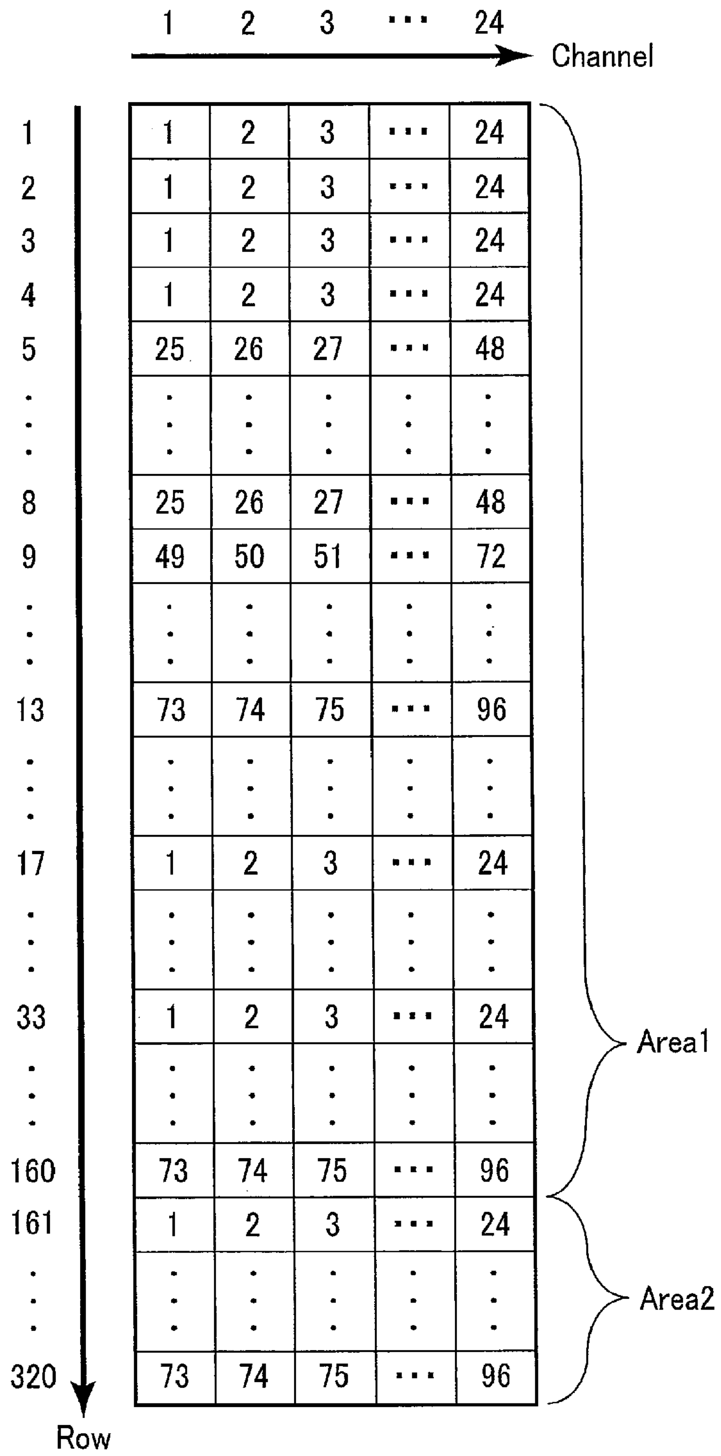
FIG. 5 is a diagram illustrating an example of readout switches which turn into an OFF state in the data acquisition processing of FIG. 3.

FIG. 5 is a diagram illustrating an example of readout switches 122 which turns into the OFF state in the data acquisition processing according to the present embodiment. In the example of FIG. 5, the plurality of X-ray detection elements 121 corresponding to the plurality of readout switches 122 are arranged in 24 channels and 320 rows in the channel direction and the row direction. Numbers shown in positions corresponding to the plurality of X-ray detection elements 121 indicate ordinal numbers of the corresponding readout switches 122 to be turned into the OFF state in the offset acquisition view. Ordinal numbers of offset acquisition views in which corresponding readout switches 122 is turned into the OFF state.

In each offset data acquisition view, offset data is acquired, for example, for each line. Each line is a block of a plurality of the X-ray detection elements 121 connected to one A/D convertor 183. Therefore, in each offset data acquisition view, a plurality of the readout switches 122 are sequentially turned into the OFF state for each line.

In the example shown in FIG. 5, one A/D convertor sequentially A/D-converts electric signals which are read out from, for example, 40 X-ray detection elements 121, within one view. Specifically, the A/D convertor 183 includes an A/D convertor connected to a plurality of the X-ray detection elements 121 contained in the first area Area1 of 1st to 160th rows, and an A/D convertor connected to a plurality of the X-ray detection elements 121 contained in the second area Area1 of 161th to 320th rows. In the first offset data acquisition view, within the first area Area1, with respect to the channel 1, readout switches 122 in 1st-4th, in 17-20th, in 33-36th, in 49-52th, in 65-68th, in 81-84th, in 96-99th, in 112-115th, in 128-131th, and in 144-147th rows are sequentially turned into the OFF state. The same goes for the second area Area2. In the second offset data acquisition view, with respect to the channel 2, readout switches 122 are sequentially turned into the OFF state in the same way. The number of X-ray detection elements 121 connected to one A/D convertor may be set to an arbitrary number according to a configuration.

In this way, the acquisition of offset data according to the present embodiment is performed during continuous scanning while a plurality of the readout switches 122 are sequentially turned into the OFF state for each line. On the other hand, projection data is acquired by X-ray detection elements 121 other than the X-ray detection elements 121 that are targets of the offset data acquisition, even in the view in which offset data is acquired by the X-ray detection elements 121 that are targets of the offset data acquisition. By the way, turning a readout switch 122 into the OFF state can be represented as disconnecting the connection between the A/D convertor 183 and an X-ray detection element 121 (PDA's pixel) which are connected with the readout switch 122. Similarly, each pixel can be represented as being disconnected with the A/D convertor 183 in sequence while the view is being shifted during acquisition of offset data.

In a case where offset data is acquired as described above, projection data is missed relative to the X-ray detection element 121 connected with the readout switch 122 turned into the OFF state. To deal with this, reconstruction processing performed by the X-ray computed tomography apparatus 1 according to the present embodiment includes processing for interpolation of missing projection data. FIG. 6 is a flowchart showing an example of reconstruction processing performed by the X-ray computed tomography apparatus 1 according to the present embodiment.

In step S21, the processing circuitry 44 implementing the image generating function 442 determines whether the view is a view in which offset data is acquired. This determination is performed in step S16 of the data acquisition processing, based on an interpolation trigger signal which is output by the readout control circuitry 181 or on a log recorded in the memory 41 or the like. The process proceeds to step S22 if it is determined that the view is a view in which offset data is acquired, and proceeds to step S23 if not.

In step S22, the processing circuitry 44 implementing the image generating function 442 interpolates missing data. The missing data can be represented as projection data corresponding to the X-ray detection element 121 connected to the readout switch 122 which is turned into the OFF state in association with acquisition of offset data. Specifically, the processing circuitry 44 implementing the image generating function 442 linearly interpolates the missing data based on projection data of X-ray detection elements 121 on both sides of the X-ray detection element 121 turned into the OFF state.

Interpolation of projection data is not limited to linear interpolation, and may be performed by nonlinear interpolation, may be performed by iterative approximation reconstruction, may be performed by using a machine learning model, or may be performed by estimation of missing projection data. Further, the interpolation of projection data may be performed by using projection data acquired in an adjacent view.

In step S23, the processing circuitry 44 implementing the image generating function 442 executes the reconstruction processing. The processing circuitry 44 implementing the image generating function 442 performs offset correction on the projection data when executing the reconstruction processing. In the offset correction, the processing circuitry 44 implementing the image generating function 442 subtracts the average value of offset data for each line from output of the A/D convertor 183 in 100 views before and after the offset data acquisition view, for example. After the offset correction, the processing circuitry 44 prepares sets of offset data and projection data corresponding to views required for the image reconstruction. For example, offset data or projection data corresponding to views of 360 degrees back from the current view is read out from memory 41. Then, the processing circuitry 44 generates CT image data by performing reconstruction calculation based on the data set corresponding to 360 degrees.

Alternatively, offset correction may be correction which subtracts moving average values about a plurality of offset data acquisition views, instead of the average value for each line, from output of the A/D convertor 183.

In step S24, the processing circuitry 44 implementing the image generating function 442 determines whether reconstruction processing for all the views is completed. If it is not determined that the reconstruction processing for all the views is completed, the process returns to step S21, and repeats processing of step S21 through step S24. If it is determined that the reconstruction processing for all the views is completed, the process terminates the data reconstruction processing.

In this way, in the X-ray computed tomography apparatus 1 according to the present embodiment, the readout control circuitry 181 turns readout switches 122 into the OFF state and acquires offset data in views in continuous scanning. Instead of projection data which is output by the A/D convertor 183 in a state where the readout switch 122 is ON, the offset data is acquired. The offset data can also be represented as data which is output by the A/D convertor 183 in a state where the readout switch 122 is OFF. According to this configuration, time for acquisition of offset data is not limited to before and after a scan and within a surplus time. Thus, according to this technique, sufficient offset data can be acquired even during a scan, and therefore there is an advantage that offset correction can be accurately performed even with respect to large drift of offset during a scan or drift that occurs during long-time scanning. The improvement of the accuracy of offset correction contributes to the improvement of image quality.

In the X-ray computed tomography apparatus 1 according to the present embodiment, the processing circuitry 44 implementing the image generating function 442 performs reconstruction processing by interpolating projection data missed in association with acquisition of offset data. Further, the readout control circuitry 181 turns readout switches 122, which are selected so as to make interpolation easy, for example, selected for each line, into the OFF state, and then acquires offset data. According to this configuration, there is an advantage that missing projection data can be easily interpolated while its influence on the image quality is suppressed.

First Modification

Hereinafter, a radiation diagnostic apparatus according to the first modification will be described with reference to the drawings. Differences from the embodiment will be mainly described here. In the description below, structural elements having the same or substantially the same functions as those of the embodiment are denoted by like reference numerals, and an overlapping description will be given only where necessary.

The order and arrangement of readout switches 122 to be turned into the OFF state in data acquisition processing are not limited to those described above with reference to FIG. 5. FIG. 7 is a diagram illustrating another example of readout switches 122 which turns into the OFF state in the data acquisition processing of FIG. 3.

As shown in FIG. 7, in an X-ray computed tomography apparatus 1 according to the present modification, offset data in a plurality of lines is acquired for each view. In the example shown in FIG. 7, in the first offset data acquisition view, offset data is acquired in six lines: channels 1, 5, 9, 13, 17 and 21 at the same time. In the same manner, in the next offset data acquisition view, offset data is acquired in lines of channels 2, 6, 10, 14, 18 and 22.

The arrangement of the lines on which offset data is acquired simultaneously may be, for example, two or more lines apart from each other, and can be arbitrarily set. Lines on which offset data is acquired simultaneously are one example of X-ray detection element rows. If lines are separated from each other by two or more channels, the linear interpolation can be easily performed even if their offset data is acquired simultaneously. That is, the arrangement of lines on which offset data is simultaneously acquired may also be represented as only an arrangement where interpolation of missing data is allowed with the image quality ensured. In other words, if interpolation of missing data is allowed with the image quality ensured, offset data may be acquired simultaneously from X-ray detection elements 121 in adjacent lines.

Even with such a configuration, the same effects as those of the above described embodiment can be achieved.

Second Modification

Hereinafter, a radiation diagnostic apparatus according to the second modification will be described with reference to the drawings. Differences from the embodiment will be mainly described here. In the description below, structural elements having the same or substantially the same functions as those of the embodiment are denoted by like reference numerals, and an overlapping description will be given only where necessary.

In the above described embodiment, the X-ray computed tomography apparatus 1 configured to read out electric signals from the X-ray detector 12 in the sequential readout method has been described as an example. On the other hand, the present technique is also applicable to an X-ray computed tomography apparatus 1 configured to read out electric signals from the X-ray detector 12 in a simultaneous readout method.

Figure 8:
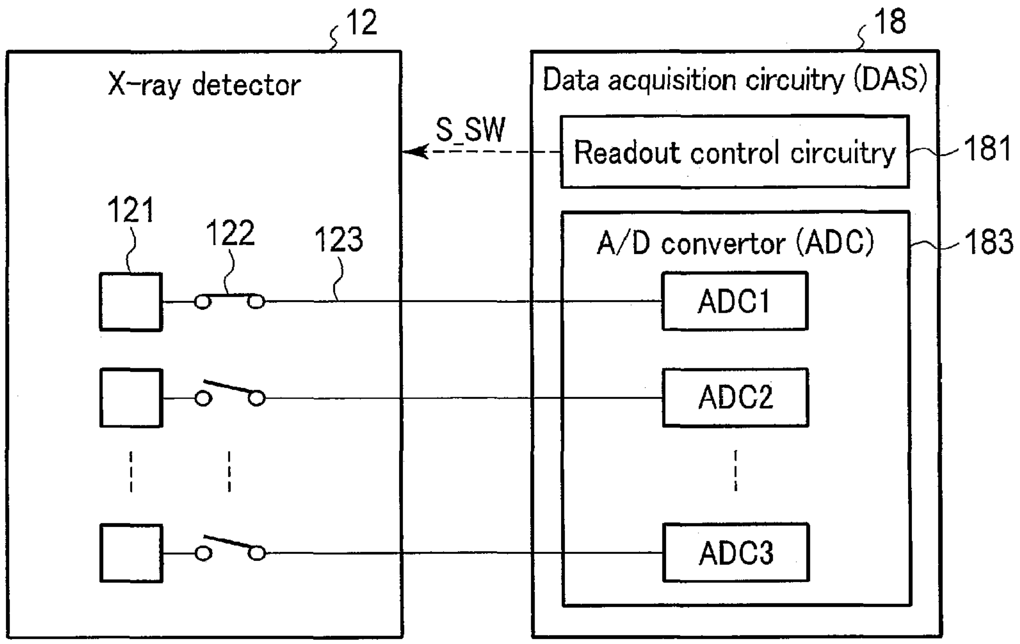
FIG. 8 is a diagram illustrating another example of a configuration of components related to acquisition of offset data in the X-ray computed tomography apparatus of FIG. 1.

FIG. 8 is a diagram illustrating an example of a configuration of components related to acquisition of offset data in the X-ray computed tomography apparatus 1 according to the present embodiment. As shown in FIG. 8, a plurality of X-ray detection elements 121 are connected to a plurality of A/D convertor 183 via a plurality of readout switches 122, respectively. Thus, the A/D convertor 183 is provided for each X-ray detection element 121.

Figure 9:
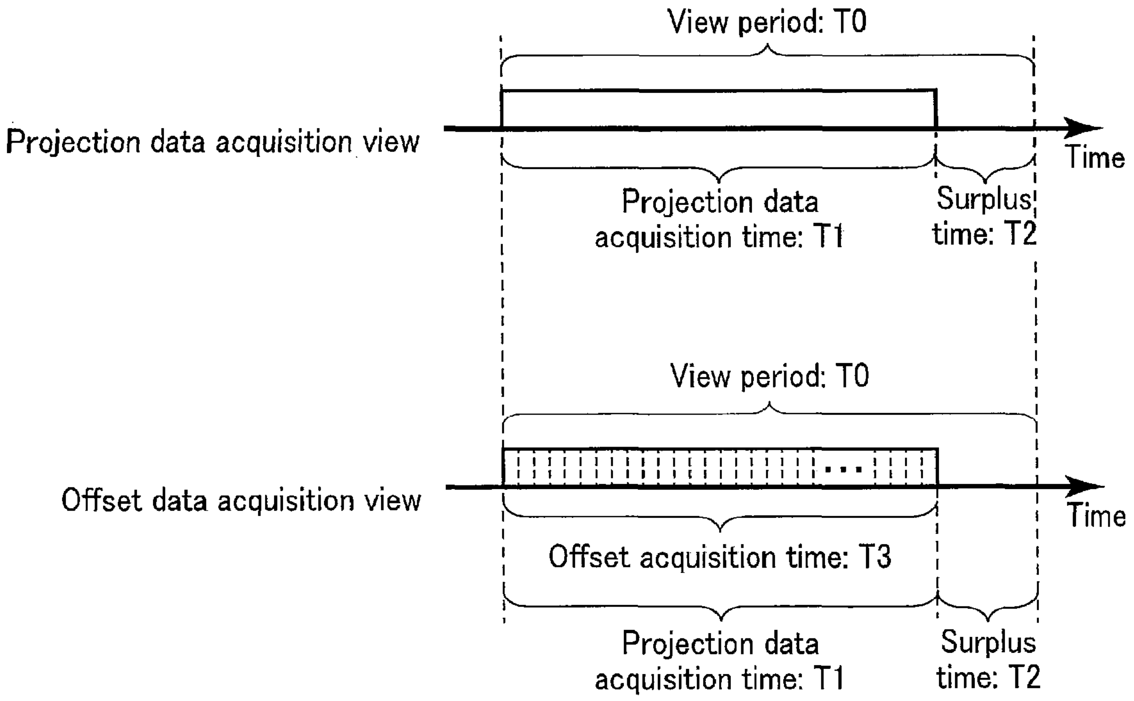
FIG. 9 a diagram illustrating an example of a time of acquisition of offset data performed in the configuration of FIG. 8.

A time of acquisition of offset data according to the present modification will now be described with reference to FIG. 9. FIG. 9 is a diagram illustrating an example of a time of acquisition of offset data in the X-ray computed tomography apparatus 1 according to the present modification. As shown in FIG. 9, in an offset data acquisition view, offset data acquisition time T3 is provided at timing corresponding to projection data acquisition time T1 in a projection data acquisition view. Specifically, in the X-ray computed tomography apparatus 1 according to the present modification, at timing when electric signals are read out from a predetermined number of X-ray detection elements 121 in the view for acquisition of projection data, readout switches 122 connected to the predetermined number of X-ray detection elements 121 are turned into the OFF state simultaneously. The readout control circuitry 181 acquires, as offset data, output of a plurality of A/D convertors 183 at a time when the readout switches 122 is in the OFF state.

X-ray detection elements 121 from which offset data is acquired simultaneously may be any X-ray detection elements 121 which are spaced apart from each other, for example, by two or more X-ray detection elements, and can be arbitrarily specified. A set of X-ray detection elements 121 from which offset data is acquired simultaneously is an example of X-ray detection element rows or X-ray detection element groups. If X-ray detection elements are separated from each other by two or more elements, the linear interpolation can be easily performed even if their offset data is acquired simultaneously. That is, the arrangement of the X-ray detection elements 121 from which offset data is acquired simultaneously can also be represented as only an arrangement where interpolation of missing data is allowed with the image quality ensured. In other words, if interpolation of missing data is allowed with the image quality ensured, offset data may be acquired simultaneously from X-ray detection elements 121 adjacent to each other.

Even with such a configuration, the same effects as those of the above described embodiment can be achieved.

Each of the plurality of A/D convertors 183 according to the present embodiment is configured to read out an electric signal of one X-ray detection element 121 for each view. However, output of offset data by each of the plurality of A/D convertors 183 may be performed once per view, or may be performed two or more times per view by oversampling. Since the readout switch 122 is in the OFF state when offset data is acquired, the parasitic capacitance to the A/D convertor 183 is smaller than that during projection data acquisition. Therefore, at the time of offset data acquisition, the operation speed of the A/D convertor 183 is higher than that at the time of projection data acquisition. Therefore, according to the present technique, more offset data can be acquired by oversampling, so that the accuracy of offset correction can be further improved.

Third Modification

In the above described embodiment, the X-ray computed tomography apparatus 1 which acquires offset data at timing corresponding to the projection data acquisition time T1 has been described as an example. On the other hand, the offset data acquisition time T3 may be shorter than the projection data acquisition time T1. The offset data acquisition time T3 is only required to be a time in which offset data necessary for ensuring sufficient accuracy of offset correction can be acquired. The present technique is a technique able to acquire offset data instead of projection data during a scan by turning any suitable readout switch 122 into the OFF state. In addition, the accuracy of offset correction varies depending on the amount of offset data. Therefore, it is preferable that the offset data acquisition time T3 is longer that the surplus time T2. Even with such a configuration, the same effects as those of the above described embodiment can be achieved. The technique according to the present modification may be combined with the technique according to the first modification or the second modification.

It is apparent that the same effect can be obtained even if the offset data acquisition time T3 is less than the surplus time T2 as long as sufficient accuracy of offset correction can be ensured.

Fourth Modification

In the above described embodiment, the X-ray computed tomography apparatus 1 which acquires offset data at timing corresponding to the projection data acquisition time T1 has been described as an example. On the other hand, the offset data acquisition time T3 may be longer than the projection data acquisition time T1. Thus, an X-ray computed tomography apparatus 1 according to the fourth modification can acquire more offset data than that of the above described embodiment. This configuration can achieve an effect that the offset accuracy can be further improved. The technique according to the present modification may be combined with the technique according to the first modification or the second modification.

Fifth Modification

In the above described embodiment, in an offset data acquisition view, the X-ray computed tomography apparatus 1 which acquires offset data by turning readout switches 122 into the OFF state for each of predetermined blocks such as lines has been described as an example. On the other hand, in an offset data acquisition view, all the readout switches 122 may be turned off to acquire offset data. In this case, interpolation of missing data can also be represented as interpolation of the missing view. Interpolation of missing data may be performed by iterative approximation reconstruction, may be performed by a machine learning model, or may be performed by estimation of missing projection data. Even with this configuration, the same effects as those of the above can be achieved. The technique according to the present modification may be combined with the technique according to each of the above described modifications.

Sixth Modification

Hereinafter, a radiation diagnostic apparatus according to the sixth modification will be described with reference to the drawings. Differences from the embodiment will be mainly described here. In the description below, structural elements having the same or substantially the same functions as those of the embodiment are denoted by like reference numerals, and an overlapping description will be given only where necessary.

In the above described embodiment, the X-ray computed tomography apparatus 1 which interpolates missing data by linear interpolation using projection data with respect to adjacent X-ray detection elements 121 has been described as an example. On the other hand, interpolation of missing data may be performed by using a machine learning model 411.

The X-ray computed tomography apparatus 1 according to the present modification will be described in detail with reference to the drawings. FIG. 10 is a diagram illustrating interpolation of missing data using the machine learning model 411 in reconstruction processing according to the present modification. In the example shown in FIG. 10, various kinds of information to be input/output are indicated by dashed lines.

As shown in FIG. 10, the machine learning model 411 is a composite function with a parameter which is learned such that the second reconstructed image is input and the first reconstructed image is output. The composite function with a parameter is defined by a combination of a plurality of adjustable functions and parameters. The parameter is a generic term for a weighting matrix and a bias. The machine learning model 411 is a composite function with a parameter, such as a Deep Neural Network (DNN). The machine learning model 411 is recorded in, for example, in a memory 41.

In the example shown in FIG. 10, the first reconstructed image is a reconstructed image which is an image reconstructed based on the first projection data set. The first projection data set includes projection data set corresponding to m1 views. The second reconstructed image is a reconstructed image which is an image reconstructed based on the second projection data set. The second projection data set includes projection data set corresponding to n1 views. It is assumed that m1 and n1 are numbers each satisfying relationship m1>n1. In other words, the second reconstructed image can be represented as a reconstructed image which is an image reconstructed based on projection data set of fewer views than of the first reconstructed image.

In a learning phase or a reinforcement learning phase, processing circuitry 44 implementing an image generating function 442 generates the first reconstructed image by performing reconstruction processing based on the first projection data set. Further, the processing circuitry 44 implementing the image generating function 442 generates the second reconstructed image by performing reconstruction processing based on the second projection data set. The second projection data set is generated, for example, by thinning out projection data set corresponding to a predetermined number of views, from the first projection data set. The machine learning model 411 achieves learning or reinforcement learning using the first reconstructed image and the second reconstructed image.

In an operation phase, the processing circuitry 44 implementing the image generating function 442 generates the second reconstructed image by performing reconstruction processing based on the second projection data set acquired in an offset data acquisition view. Therefore, from the second projection data set in the operation phase, projection data has been missed due to offset data acquisition. The number of views n2 of projection data set included in the second projection data set in the operation phase may be the same as or different from the number of views n1 of projection data set included in the second projection data set in the learning phase or reinforcement learning phase. The processing circuitry 44 implementing the image generating function 442 generates the first reconstructed image using the generated second reconstructed image and the machine learning model 411. In other words, the first reconstructed image in the operation phase can be represented as a reconstructed image in which projection data missed due to offset data acquisition is interpolated.

In addition, reinforcement learning of the machine learning model 411 may be performed based on: the second reconstructed image which is an image reconstructed based on the second projection data set from which projection data has been missed; and the first reconstructed image which is output by the machine learning model 411 receiving the second reconstructed image as input.

The X-ray computed tomography apparatus 1 according to the present modification further includes a memory 41 which stores the machine learning model 411. The machine learning model 411 achieves learning or reinforcement learning based on: the first reconstructed image which is an image reconstructed based on the first projection data set of the predetermined number of views; and the first reconstructed image which is an image reconstructed based on the second projection data set of a fewer number of views than the predetermined number of views. The processing circuitry 44 implementing the image generating function 442 generates the first reconstructed image in which missing data is interpolated, using projection data set in which projection data or projection data set is missed due to acquisition of offset data, and the machine learning model 411. Even with this configuration, the same effects as those of the above can be achieved. The technique according to the present modification may be combined with the technique according to each of the above described modifications.

The processing circuitry 44 may include circuitry which has learned a parameter such that the second reconstructed image is input and the first reconstructed image is output and which achieves a similar function to the machine learning model according to the present modification. For example, such circuitry is achieved by an integrated circuit such as an ASIC or a PLD.

The memory 41 in which such circuitry and the machine learning model 411 are stored may be provided outside the X-ray computed tomography apparatus 1.

Seventh Modification

In the above described embodiment, the X-ray computed tomography apparatus 1 which interpolates missing data by linear interpolation using projection data with respect to adjacent X-ray detection elements 121 has been described as an example. On the other hand, interpolation of missing data may be performed by estimating the missing projection data. For example, the processing circuitry 44 implementing the image generating function 442 calculates the projection data in a pseudo manner based on an imaging condition, information related to the subject, and the like. Various information used for pseudo calculation of the projection data is stored in, for example, the memory 41. In other words, the processing circuitry 44 implementing the image generating function 442 can be represented as circuitry estimating the missing projection data. The processing circuitry 44 implementing the image generating function 442 performs image reconstruction using acquired projection data set and estimated projection data set, to generate an interpolated reconstructed image. Even with this configuration, the same effects as those of the above can be achieved. The technique according to the present modification may be combined with the technique according to each of the above described modifications.

Eighth Modification

In the above described embodiment, the X-ray computed tomography apparatus 1 which interpolates missing data by linear interpolation using projection data with respect to adjacent X-ray detection elements 121 has been described as an example. On the other hand, interpolation of missing data may be performed by iterative approximation reconstruction. For example, the processing circuitry 44 implementing the image generating function 442 performs iterative approximation reconstruction using projection data set in which projection data is missed in association with acquisition of offset data. Even with this configuration, the same effects as those of the above can be achieved. The technique according to the present modification may be combined with the technique according to each of the above described modifications.

According to at least one embodiment described above, the accuracy of offset correction can be improved.

The term "processor" used in the above description means, for example, a circuit such as a CPU, a CPU, an application specific integrated circuit (ASIC), or a programmable logic device (PLD). The PLD includes a Simple programmable logic device (SPLD), a complex programmable logic device (CPLD), and a field programmable gate array (FPGA). The processor implements a function by reading and executing a program stored in a storage circuit. The program may be directly incorporated into the circuit of the processor instead of being stored in the storage circuit. In this case, the processor implements the function by reading and executing the program incorporated into the circuit. Instead of executing the program, the function corresponding to the program may be implemented by a combination of logic circuits. Each processor of the above described embodiment is not limited to being implemented as a single circuit for each processor, but may be implemented as one processor by combining a plurality of independent circuits to achieve their functions. Further, a plurality of components shown in FIG. 1, FIG. 2 and FIG. 8 may be integrated into one processor to achieve their functions.

Furthermore, the functions described in connection with the above embodiments may be implemented, for example, by installing a program for executing the processing in a computer, such as a work station, etc., and expanding the program in a memory. The program that causes the computer to execute the processing can be stored and distributed by means of a storage medium, such as a magnetic disk (a hard disk, etc.), an optical disk (CD-ROM, DVD, etc.), and a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:

an X-ray detection array including a plurality of X-ray detection elements arranged in a slice direction and a channel direction;

an A/D convertor array including a plurality of A/D convertors which A/D-convert an electric signal output from the plurality of X-ray detection elements;

a plurality of readout switches which switch connections between the plurality of X-ray detection elements and the plurality of A/D convertors; and readout control circuitry which, with regard to a first X-ray detection element block of the plurality of X-ray detection elements, acquires, in a first view during a scan, projection data and does not acquire offset data by setting a first readout switch to ON, and acquires, in a second view at a different time from the first view during the scan, offset data and does not acquire projection data by setting the first readout switch to OFF, wherein, with regard to a second X-ray detection element block of the plurality of X-ray detection elements, the readout control circuitry acquires, in the first view, the offset data and does not acquire the projection data by setting a second readout switch to OFF, and acquires, in the second view, the projection data and does not acquire the offset data by setting the second readout switch to ON.

2. The X-ray computed tomography apparatus according to claim 1, wherein the readout control circuitry acquires the offset data when a predetermined time elapses from start of the scan during the scan.

3. The X-ray computed tomography apparatus according to claim 1, wherein the readout control circuitry acquires the offset data when a variation amount of a temperature or output of any A/D convertor exceeds a predetermined threshold during the scan.

4. The X-ray computed tomography apparatus according to claim 1, wherein the readout control circuitry acquires the offset data at a preset certain cycle during the scan.

5. The X-ray computed tomography apparatus according to claim 1, wherein the first X-ray detection element block is all of the X-ray detection elements.

6. The X-ray computed tomography apparatus according to claim 1, wherein acquisition time of the offset data in the second view is longer than surplus time in the first view.

7. The X-ray computed tomography apparatus according to claim 1, wherein pieces of the offset data acquired in the second view is greater in number than pieces of the projection data acquired in the first view.

8. The X-ray computed tomography apparatus according to claim 1, further comprising processing circuitry which interpolates projection data missed by acquisition of the offset data, to perform image reconstruction.

9. The X-ray computed tomography apparatus according to claim 1, wherein the plurality of A/D convertors are provided for respective of the plurality of X-ray detection elements, and wherein the readout control circuitry sequentially changes the readout switches to be turned ON over the plurality of X-ray detection elements to sequentially read out projection data or the offset data.

10. The X-ray computed tomography apparatus according to claim 1, wherein the plurality of A/D convertors are provided for respective of the plurality of X-ray detection elements, and wherein the readout control circuitry turns the readout switches with respect to a bank of a plurality of the X-ray detection elements into an ON state simultaneously, and reads out projection data or the offset data with respect to the bank of the plurality of X-ray detection elements simultaneously.

11. The X-ray computed tomography apparatus according to claim 8, wherein the readout control circuitry outputs information for identifying the second view, to the processing circuitry.

12. The X-ray computed tomography apparatus according to claim 8, wherein in the second view, when the offset data with respect to the first X-ray detection element block is acquired, the processing circuitry linearly interpolates the missed projection data based on projection data acquired with respect to the second X-ray detection element block adjacent to the included X-ray detection element block.

13. The X-ray computed tomography apparatus according to claim 8, further comprising a memory which stores a machine learning model learned using a first reconstructed image based on a projection data set of a predetermined number of views and a second reconstructed image based on a projection data set of a fewer number of views than the predetermined number, the processing circuitry generates the first reconstructed image based on a projection data set from which the second view is missed, and generates the second reconstructed image using the generated first reconstructed image and the machine learning model.

14. The X-ray computed tomography apparatus according to claim 8, wherein by an iterative approximation reconstruction method, the processing circuitry interpolates a projection data set of the second view, to perform the image reconstruction.

15. The X-ray computed tomography apparatus according to claim 8, wherein the processing circuitry estimates a projection data set of the second view based on an imaging condition, and interpolates a projection data set from which the second view is missed using the estimated projection data set, to perform the image reconstruction.

* * * * *